United States Patent [19]

Troutner et al.

[11] Patent Number: 4,615,876

[45] Date of Patent: Oct. 7, 1986

[54] MACROCYCLIC COMPLEXES OF TECHNETIUM-99M FOR USE AS DIAGNOSTIC RADIONUCLIDES

[75] Inventors: David E. Troutner; Wynn A. Volkert, both of Columbia, Mo.

[73] Assignee: Curators of the University of Missouri, Columbia, Mo.

[21] Appl. No.: 488,184

[22] Filed: Apr. 25, 1983

[51] Int. Cl.$^4$ .................. A61K 43/00; A61K 49/00
[52] U.S. Cl. ........................... 424/1.1; 424/9; 534/14
[58] Field of Search ............... 424/1.1, 9; 260/429 R, 260/429 J

[56] References Cited

U.S. PATENT DOCUMENTS

| | | | |
|---|---|---|---|
| 4,352,751 | 10/1982 | Wieder et al. | 424/1.1 |
| 4,360,511 | 11/1982 | Baldwin et al. | 424/1.1 |
| 4,363,793 | 12/1982 | Blau et al. | 424/1.1 |

OTHER PUBLICATIONS

Karesh et al, J. Pharmaceutical Sciences, 66 (1977) 225-8.
Eckelman et al. J. Pharmaceutical Sciences, 64 (1975) 704-6.

*Primary Examiner*—Christine M. Nucker
*Attorney, Agent, or Firm*—Tilton, Fallon, Lungmus & Chestnut

[57] ABSTRACT

Stable neutral-lipophilic complexes of technetium-99m (Tc-99m) useful as diagnostic radionuclidic imaging agents are formed by complexing technetium-99m pertechnetate with alkylene amine oximes (viz. propylene amine oxime) in aqueous solutions under reducing conditions. The complexes have a zero charge, contain an O—H—O ring closure bond, and are sufficiently stable for parental administration in imaging by scintillation scanning. Substituents can be attached to the $C_2$ to $C_4$ alkylene carbon backbone of the tetradentate amine oxime ligands to structurally modify them and produce a variety of Tc-99m-radiopharmaceuticals with specific body imaging applications.

8 Claims, No Drawings

4,615,876

MACROCYCLIC COMPLEXES OF TECHNETIUM-99M FOR USE AS DIAGNOSTIC RADIONUCLIDES

GRANT REFERENCE

The present invention was developed in part under the following federal grants:

NIH; #CA33526-02; "Developing Macrocyclic Amines as Tc-99m Imaging Agents"; Investigators: Dr. W. A. Volkert (PI), D. E. Troutner (Co-PI) and R. A. Holmes.

Veterans Administration Medical Research Div.; "Tc-99m Labeled Cyclam: A Basis for New Radiopharmaceuticals"; Investigators: Drs. Holmes (PI), D. E. Troutner and W. A. Volkert.

BACKGROUND AND PRIOR ART

The field of this invention relates to radionuclides employed in diagnostic nuclear medicine, particularly the gamma emitting diagnostic agents for imaging by scintillation scanning. More particularly, this invention is concerned with the radionuclide technetium-99m which when chelated by certain ligands produces clinically useful radiopharmaceuticals. Tc-99m has nearly ideal physical properties for scintigraphic imaging techniques and, despite limited specificity of previously available ligands when complexed to Tc-99m, is the most frequently used radionuclide for imaging in diagnostic nuclear medicine. For most in vivo uses, the metal, which is available as pertechnetate, must be complexed in a reduced form by ligands which produce complexes that are stable in aqueous solutions and body fluids and, which, if properly structured, display specific biodistributions.

The chemical synthesis of ligands that form Tc-99m complexes with improved properties has been hindered by several factors. Pertechnetate ($TcO_4^-$-99m) is readily available but only in extreme dilutions. For example, the commonly employed molybdenum-99 (Mo-99) generator, which produces Tc-99m as a radioactive decay product, is in the form of an alumina column that is eluted with aqueous sodium chloride to produce the pertechnetate solutions in the range of $10^{-6}$ to $10^{-9}$ molar concentration. Such dilutions make it very difficult to study the reactions involved in chelate formation, or to chemically and structurally characterize the resulting coordination complexes. Furthermore, the chemistry of technetium itself is poorly understood.

Although Tc-99m chelates have provided a variety of clinically useful radiopharmaceuticals for diagnostic imaging, producing suitable Tc-99m-compounds with high physiological and organ selectivity is a complex task. Certain constraints limit the number of chelating ligands that would be appropriate for formulating new diagnostic agents labeled with Tc-99m. Since Tc-99m has only a 6 hr half-life, stable Tc-99m chelates must be produced rapidly (under sterile, apyrogenic conditions) in high yields in neutral aqueous solutions so that they may be readily available to all clinical Nuclear Medicine laboratories. In addition, the ligands must show no adverse toxicity for routine use as diagnostic agents in human studies.

All Tc-99m-chelates so far approved by the FDA for routine use in Nuclear Medicine have overall negative or positive charges. Most ligands used to complex Tc-99m in high yields in aqueous media contain O, N, S, or P donor atoms. These complexes are very useful for evaluating the functional status of human tissues or organs in which a charged species would be advantageous (i.e., kidney filtration, hepatobiliary function by the anionic or cationic clearance pathway, brain imaging involving the breakdown of the blood-brain-barrier (BBB), cation localization in heart muscle, bone uptake or phosphonate chelates, etc.) Charged hydrophobic complexes are not now routinely available to evaluate biological functions where the Tc-99m-chelate must passively diffuse across cell walls or the intact BBB. The most clinically applicable agent for these latter applications would be a stable neutral-hydrophobic Tc-99m chelate that would lead to the design of a series of new diagnostic radiopharmaceuticals.

An area where a suitable neutral-hydrophobic Tc-99m-chelate would find immediate diagnostic application is to assess regional cerebral blood flow (rCBF) in humans. The need for this type of Tc-99m labeled agent has been recognized for some time. See Oldendorf, *J. Nucl. Med.*, 19, 1182, Letters to Ed (1978). As stated by Dr. Oldendorf: "I believe that a concerted effort should be made to develop a Tc-99m labeled compound which is sufficiently lipid-soluble that it would undergo complete clearance in one pass through the brain".

Compounds labeled with short-lived positron emitters (e.g., C-11, O-15 and F-18) have been used to successfully delineate rCBF in normal and diseased brain tissue using Positron Emission Transaxial Tomography in a limited number of Nuclear Medicine laboratories. The costs to produce these compounds (including an on-site medical cyclotron) are prohibitive for wide spread use. If we are to witness the performance of such studies in the daily practice of medicine, the development of agents capable of rCBF assessment but labeled with more available and less costly radionuclides emitting a single photon (i.e., a γ-ray), such as Tc-99m is highly desirable.

Two types of single photon emitting diagnostic agents have been used to assess brain blood flow patterns in humans. The first is best exemplified by Xe-133, an inert noble gas, that passively diffuses across the BBB and clears the tissue at a rate proportional to the blood flow through that tissue. The pattern of rCBF is determined by following the rate of Xe-133 clearance as a function of time at different sites of the brain using either a specialized Single Photon Emission Computed Tomographic (SPECT) instrument (1) or a commercial multidetector system (2). The second class of compounds include those that passively diffuse across the BBB (with a high extraction efficiency) into the brain and become trapped in the brain tissue. The trapping allows time for determination of rCBF patterns by more conventional SPECT imaging devices. The two most widely used single photon brain perfusion agents of this latter type are: I-123-N,N,N'-trimethyl-N-(2-OH-3-methyl-5-iodobenzyl)-1,3-propanediamine,(I-123-HIPDM) (3) and I-123-Iodoamphetamine, (I-123-IMP) (4,5). Because Tc-99m has superior imaging properties and is more readily available and less expensive, any new Tc-99m labeled compounds with similar or even better capabilities for brain uptake (and/or washout) as Xe-133, I-123-IMP or I-123-HIPDM would find widespread clinical applicability.

Besides rCBF studies these neutral-lipophilic Tc-99m-chelates would also be desirable in imaging the lungs. I-123-iodoantipyrene is a hydrophobic compound that distributes following injection throughout the lung water and has been used to assess extravascular lung water (EVLW) in normal and disease states (6). This agent passively diffuses into the lung parenchyma and is washed out by pulmonary blood flow. Lung imaging has also been performed using I-123-IMP by J. Tonya, et al., (7). I-123-IMP is taken up by lung tissue and slowly released, presumably due to its binding to intracellular low specificity, - high capacity endothelial amine receptors. Clearly, Tc-99m agents that exhibit properties similar to I-123-iodoantipyrene would have value for measuring regional EVLW imaging (particularly in patients with the acute respiratory distress syndrome (6)). Likewise, a Tc-99m-compound that binds to amine receptors in the lung would be useful for assessing what Tonya et al. (7) describe as "metabolic lung imaging".

Imaging of heart muscle in patients with myocardial damage using fatty acids or fatty acid analogues labeled with positron emitters (8) or I-123 has shown promise as a diagnostic tool (9). As indicated earlier, the high cost of producing compounds labeled with positron emitters precludes their widespread availability in the foreseeable future.

Under normoxic conditions the energy requirements of heart muscle are met by oxidation of fatty acids and, therefore, the extraction of free fatty acids by the normal myocardium is high. In areas of heart muscle damage where local $pO_2$ is decreased (eq. ischemia) fatty acid oxidation (i.e., $\beta$-oxidation) and free fatty acid uptake is decreased (10). Regional fatty acid metabolism could be measured by determining the rate of clearance of the labeled fatty acid from the myocardium. Alternatively, a fatty acid analogue that enters the metabolic pathway, undergoes partial metabolism, and whose radioactive label is trapped within the myocardium would also reflect regional metabolic activity (i.e., similar to 18-F-fluorodeoxyglucose for brain metabolic images (11)). The localized trapped activity can then be imaged (12). Fatty acid analogues labeled in various manners with I-123 are taken up by normal heart muscle and depending upon the structure of the specific compound will either clear rapidly following intracellular $\beta$-oxidation (similar to C-11 labeled fatty acids) or can be structurally modified so they will be trapped by the myocardial tissue (13,14). I-123 can be attached directly to the $\omega$-end (i.e., the end opposite the carboxylic acid group) of the alkyl-chain or attached to the $\omega$-end of the alkyl chain by means of a I-123-phenyl group. Both types of derivatives have been successfully used as myocardial imaging agents (15,16). The fact that good myocardial uptake is observed with fatty acid analogues where the bulky-hydrophobic I-123-phenyl group is attached to the $\omega$-end indicates that other lipophilic groups similarly attached will have little effect on their extraction by normal heart muscle. Karesh, et al., (17) and Schneider et al., (18) failed in their attempts to produce a Tc-99m-fatty acid analogue that localizes in heart muscle. Both investigators attached ligands to the $\omega$-ends of fatty acid analogues that formed negatively charged Tc-99m-chelates and concluded that the charged chelate at the end of the alkyl chain prevented their intracellular transport. It is expected that a neutral-hydrophobic Tc-99m chelate attached to the $\omega$-end of fatty acid analogues will not prevent normal myocardial cell uptake (viz., these types of compounds would be structurally similar to the I-123-phenyl-$\omega$-fatty acid analogues).

At least three neutral Tc-99m-complexes have been prepared and reported. See, Burns, et al.; *J. Nucl. Med.*, 20, 641, 1979. Kramer, et al., Proc. 4th Int. Symp. on Radiopharmaceutical Chemistry, Julich, Germany, Aug. 23–27, 1982, p. 323–324. Yokoyama, et al., *J. Nucl. Med.*, 17, 816–19 (1976). None of these Tc-99m complexes have been established for routine diagnostic use. These neutral ligands have not met all of the needed requirements; for example, the neutral complexes of Yokoyama, et al. are extremely difficult to derivatize and use —SH groups for complexation with Tc-99m as does the neutral complex of Burns et al. Ligands utilizing —SH groups for chelation of Tc-99m form stable complexes but are difficult to store. The neutral chelate of Kramer et al., does not have desirable stability characteristics. As far as known, none of these ligands show a high extraction efficiency by the brain.

Ligands that employ only N-atoms for chelation of Tc-99m have been shown to readily form complexes in aqueous media. Tetraaza ligands and in particular macrocyclic tetraaza ligands, form very stable Tc-99m complexes. See, Troutner, et al., *J. Nucl. Med.*, 21, 443–448 (1980), which describes the complexing of $TcO_4^-$-99m with the macrocyclic tetraaza ligand, cyclam. As far as is known, the only published study showing full characterization of such a macrocyclic ligand complex of Tc was published in 1981 by Zuckman, et al., *Inorg. Chem.*, 20, 2386–2389. The complex with cyclam (1,4,8,11-tetraazacyclotetradecane) under reducing conditions was shown to produce a $TcO_2^{+1}$ core, and a resulting complex had a charge of +1.

As far as is known, the ligand specifically referred to in this disclosure as propylene amine oxime (PnAO) has not been employed to prepare a complex with Tc-99m. This ligand is 2,2'-(1,3-diaminopropane) bis (2-methyl-3-butanone) dioxime and is henceforth referred to as PnAO. Methods for preparing PnAO are well known as is its use in complexing metal ions. See, for example, Vassian, et al., (19). Complexation of PnAO to metal ions is by the 4 N-atoms and results in the liquid forming a cyclical structure around the chelated metal (20). The structural formula of PnAO is:

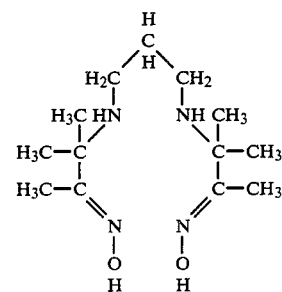

The corresponding ethylene amine oxime (EnAO) is 2,2'-(diaminoethane) bis(2-methyl-3-butanone) dioxime, and the corresponding n-butylene amine oxime (BnAO) is 2,2'-(1,4-diaminobutane) bis(2-methyl-3-butanone) dioxime.

REFERENCES 1–20

1. N. A. Lassen, et al., J. Nucl. Med., 24, 17–21, 1983.
2. B. Larsen, et al., Reg. Cereb. Bld. Flow Bull., 2, 27–31, 1981.
3. H. F. Kung, et al., J. Nucl. Med., 24, 66–72, 1983.

4. H. S. Winchell, et al., J. Nucl. Med., 21, 947–952, 1980.
5. D. Kuhl, et al., J. Nucl. Med., 23, 196–203, 1982.
6. M. Critchley, et al., Proc. Third World Cong. Nucl. Med. and Biol. Paris, France, Aug. 31–Sept. 3, 1982, pp. 2546–2549.
7. J. Tonya, et al., Proc. Third World Cong. Nucl. Med. and Biol., Paris, France, Aug. 31–Sept. 3, 1982, pp. 2554–2557.
8. M. M. Ter-Pegossian, et al., Circ., 61, 242–255, 1980.
9. C. Frundlieb, et al., J. Nucl. Med., 21, 1043–1051, 1980.
10. E. S. Weiss, et al., Circ., 55, 66–73, 1977.
11. M. Reivich, et al., Circ. Res., 44, 127, 1979.
12. E. Livini et al., J. Nucl. Med., 23, 169–175, 1982.
13. F. F. Knapp, et al., Proc. Fourth Int'l Symp. on Radiopharm. Chem., Julich, W. Ger., Aug. 23–27, 1982, pp. 53–55.
14. A. Hock, et al., J. Nucl. Med., 24, 285–296, 1983.
15. H. Roesler, et al., J. Nucl. Med., 24, 285–296, 1983.
16. P. Angelberger, et al., Prog. in Radiopharmacol., Vol. 2, Ed. by P. H. Cox, Elsevier-Hollard Biomed. Press, New York, NY, 1981, pp. 61–74.
17. S. M. Karesh, et al., J. Pharm. Chem., 66, 225, 1977.
18. R. F. Schneider, et al., Proc. Fourth Int'l Symp. on Radiopharm. Chem., Julich, W. Ger., Aug. 23–27, 1982, pp. 56–57.
19. R. K. Murmann and E. O. Schlemper, Inorg. Chem., 12, 2625, 1973.
20. E. Vassian, et al., Inorg. Chem., 6, 2143–2146, 1976.

SUMMARY OF INVENTION

This invention is based in part on the discovery that technetium-99m can be complexed (by reduction of Tc-99m-pertechnetate in aqueous media) to propyleneamine oxime, to produce a stable lipophilic complex. This complex and derivatives will make useful diagnostic imaging agents. This appears to be a general complexation reaction with this type of amine oxime ligand since two other forms of the basic tetradentate amine oxime ligand, ethyleneamine oxime (EnAO) and n-butyleneamine oxime (BnAO) also form neutral-hydrophobic Tc-99m chelates in aqueous solutions. The complexes have a zero net charge and are easily derivatizable. Tc-99m EnAO and BnAO are capable of crossing the blood-brain-barrier, passing through cell walls and being taken up efficiently by lung tissue, thereby extending their range of usefulness as radiopharmaceuticals. Further, the complexes are sufficiently stable, even in the presence of oxygen, to permit their preparation, storage and parental administration for imaging. The macrocyclic PnAO ring is closed during formation of the complex by an O—H—O band which serves to complete the ring and control the charge on the complex.

With prior art, the macrocyclic tetraamine ring is performed when Tc-99m-chelates of cyclam are made, and the resulting open chain and macrocyclic-tetraaza chelates with Tc-99m are positively charged.

Although not yet known with certainty, it is believed that the amine oxime complexes have a unique structure (compared to other complexes where Tc is chelated by 4-N atoms) with a TcO$^{+3}$ core, as distinguished from the prior art tetraamine-type chelates with TcO$_2^{+1}$ core. Apparently, in the formation of the complex, hydrogen ions are eliminated from both of the propylene amine groups, thereby resulting in the final net charge of zero.

DETAILED DESCRIPTION

The propylene amine oxime ligand starting material for preparing the complexes of this invention can be prepared by known synthetic procedures. For example, PnAO (as well as EnAO and BnAO) can be synthesized by the method of Vassian et al., (19). Briefly described, this synthesis involves the reaction of 1,3-propane diamine (1,2 ethanediamine or 1,4-n-butanediamine for EnAO or BnAO, respectively) with the chloro-oxime reagent.

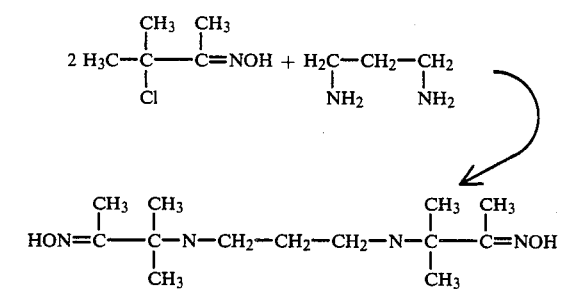

Different forms of the chloro-oxime reagent, as illustrated below, can be used to form various PnAO analogues.

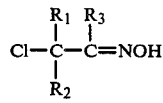

The specific reagent used to form PnAO is when $R_1=R_2=R_3=CH_3$. Other chloro-oxime reagents where $R_1$ and/or $R_2$ and/or $R_3$ are either hydrogen or small alkyl substitutes of 1–4 carbons in any combination can be used to form analogues of PnAO (or PnAO derivatives) with the same basic tetradentate ligand backbone. These PnAO analogues should be able to form Tc-99m complexes with the same basic chelate structure as Tc-99m-PnAO. Any of these chloro-oxime reagents can be synthesized by reacting NOCl with the appropriate alkene as follows:

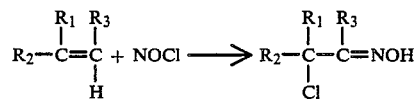

Propylene amine oxime or PnAO derivatives where substituent groups are introduced at the 2-carbon position of the propylene moiety can be prepared from diethylmalonate. A general scheme is outlined below for the synthesis by this route and involves the alkylation of the C-2 carbon followed by conversion of the diester functionalities to diamides with subsequent reduction to the 1,3-propane diamine derivative. This product can then be reacted with the chloro-oxime reagent to form the respective PnAO derivative.

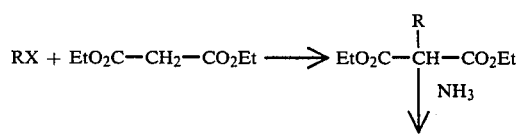

-continued

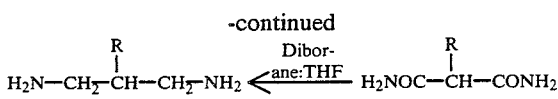

Alternatively, analogue derivatives can be made by a similar reaction where 2-OH-diethylmalonate is reacted with RX. In this case, the R group is attached to the C-2 propylene carbon by an ether linkage instead of directly to the C-2 of propylene:

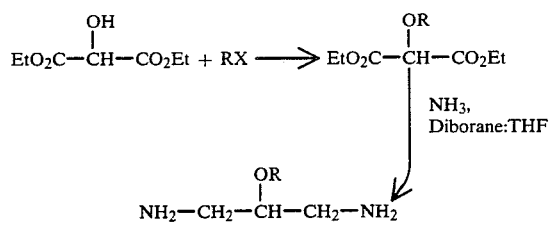

As before, the ester groups are converted to the amines and reacted with excess chloro-oxime to form the respective PnAO derivative. In the preceding formulas, R can be any of the groups previously defined for $R_1$, $R_2$, or $R_3$.

The other principal starting material is the technetium-99m as pertechnetate ($TcO_4^-$-994m). This can be purchased in aqueous solutions from commercial sources in the United States (e.g., Med-Physics Inc., Emeryville, CA). Preferably, however, the pertechnetate reagent is freshly generated as the sterile, pyrogen free eluate from a standard molybdenum-99 (Mo-99): Tc-99m radionuclide generator (e.g., Mallinckrodt Nuclear, St. Louis, MO, E.R. Squibb and Sons, New Brunswick, N.J., etc.). In accordance with standard practice, the $TcO_4^-$-99m is eluted from the column using aqueous physiological saline, such as isotonic (0.9%) NaCl. The eluate will contain a dilute solution of the pertechnetate, such as a molar concentration of about $10^{-6}$-$10^{-9}$.

The complexation reaction between the propylene amine oxime ligand and the pertechnetate reagent is carried out in an aqueous solution under reducing conditions. Standard reducing agents can be employed, such as those that have been previously used in the reduction and ligand complexing of Tc-99m in commercial "kit-type" preparations. For example, suitable reducing reagents include; $SnCl_2$ and other stannous salts, sodium dithionite, or Sn or Zr electrodes, etc. Even though Tc-99m-PnAO can be prepared by a variety of reducing conditions (for example, we have prepared Tc-99m-PnAO by reducing $TcO_4^-$-99m in physiological saline at pH 8-10 in the presence of 0.004M PnAO with sodium dithionite), stannous salts are the most convenient method of preparation. The use of stannous salts is a particularly suitable means for providing the reducing agent in pre-formulated radiopharmaceutical "kits" for routine use in patients. In these "kits", the lypholyzed contents of a sterile pyrogen free vial containing the stannous salt, complexing ligand and other chemicals, possibly a buffer and stabilizing agent, are combined with the eluate from a Mo-99-Tc-99m generator containing $TcO_4^-$-99m. The resulting Tc-99m chelate can then be injected into the blood stream of a patient.

The complexation reaction of Tc-99m with PnAO is not highly sensitive to pH as long as either high acid or basic conditions are avoided. For example, the complexation reaction can be carried out at a pH of 5 to 10. In this pH range, complexation yields of greater than 95% are achieved by reducing $TcO_4^-$-99m with stannous ion with excess PnAO in saline solution. The ligand concentration in saline at the time of $TcO_4^-$-99m addition can be as low as $10^{-5}$M. The pH adjustment can be made with a variety of reagents, such as sodium bicarbonate, sodium acetate, sodium borate, or other salts suitable for buffering in this pH range. The temperature of the reaction is not critical, and may be carried out at room temperature. However, the rate of the reaction may be promoted, if desired, by using a temperature as high as 90° C.

The desired complexing reaction occurs rapidly, and will usually be completed within 10 min. If desired, the completion of the reaction may be determined by a suitable test procedure, such as paper chromatography to determine the percent hydrolyzed reduced Tc-99m using saline as the solvent. High performance liquid chromatography (HPLC) using reverse phase chromatography is also rapid and accurate (See Example II).

Based on presently available evidence, it is believed that the Tc-99m-PnAO complex has a single component, is neutral and lipophilic and has excellent stability in aqueous solutions. The stability of this chelate is more than adequate to be formulated and used routinely for parental injections in clinical Nuclear Medicine Laboratories (See Example II, Table 3). A single symmetrical peak is observed following HPLC analysis using linear gradient elution (See Example II) of the complexes off of a Hamilton PRP-1 column. Also, electrophoresis of the chelate results only in a single peak at the origin.

Both EnAO and BnAO will also form stable complexes with Tc-99m that are lipophilic and neutral using production methods identical to those described for Tc-99m-PnAO production. These results suggest that the mechanism and type of complexes formed by the linear tetradentate amine oxime ligands are similar.

Based on presently available evidence, it is believed that the lipophilic, stable, neutral complex formed as described aove has the following structural formula:

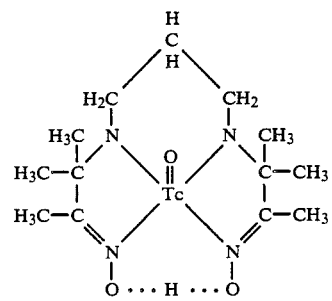

As shown more fully in the following experimental section, the foregoing formula is based on experiments carried out with Tc-99 and the unsubstituted propylene amine oxime ligand. It is believed however, that the resulting structure is the same at tracer levels with Tc-99m, and for ligands in which the propylene amine oxime group ligand is substituted with the substituents described later in this document. As will be noted, the technetium core is in the form of $TcO^{+3}$. Two hydrogens have been eliminated from the propylene amine nitrogens and one from oxime hydrogens. The resulting complex is therefore neutral. The O—H—O bond completes the macrocyclic ring. As far as is known, this type of Tc-amine oxime complex structure has not been previously described. The experimental basis of the present invention includes the following tests and results provided by Examples I–VI.

The in vivo behavior of these complexes in animals indicates their potential wide spread applicability for the formulation of new and useful radiopharmaceuticals. A bolus intravenous injection of Tc-99m PnAO in laboratory animals (i.e., mice, rats, rabbits, monkeys, and dogs) showed a high uptake by the brain and lung within a few seconds after injection. The activity in the brain decreases rapidly and becomes relatively low by 15 min. (See Example III). This uptake and washout of Tc-99m PnAO from the brains of dogs, rabbits, and rats was clearly visualized using a standard scintillation camera (Ohio Nuclear Model 120 Mobil Camera, Technicare Corp., Solon, OH) and interfaced directly to a PDP-11/40 computer. The images were digitized and processed by the computer. The activity expressed as a function of time of the Tc-99m-PnAO in the brain was evaluated by plotting the activity outlined by the region of interest (ROI) of the brain compared to an ROI over non-brain tissue against time. The rate of Tc-99m PnAO washout in the dog was similar to that observed with clearance of Xe-133 from the brain in humans (21) (See Example III). This data indicates that the brain uptake of Tc-99m-PnAO is efficient and that measurement of washout rates of this chelate from various areas of the brain with the proper instrumentation is, indeed, feasible. Furthermore, the specific SPECT instrumentation (1), multiprobe systems (2) currently used to follow the rate of Xe-133 brain clearance in humans can also be applied to determine regional clearance of Tc-99m-PnAO from the brain and determine rCBF patterns in patients. Even though less satisfactory, diagnostic information by planar imaging of the Tc-99m-PnAO uptake in the brain can also be obtained.

The extraction efficiency of Tc-99m PnAO from the plasma by the brain of rats and rabbits was determined by using a single probe external gamma-ray detection system similar to that used by M. E. Raichle, et al. (22). (See Example III). The extraction efficiency in these animals at presumed normal blood flow, was determined to be about 70–90%. The extraction efficiency was also measured in monkeys using the external probe system of Raichle et al., (22) and was found to be 80% at normal blood flow. As far as is known, this extraction efficiency is superior to any neutral or charged lipophilic Tc-99m complex known. The ability of this complex to readily diffuse across intact cellular membranes was confirmed by the observation that Tc-99m-PnAO placed into a whole-blood sample (Hct=45) will reach an equilibrium concentration of about 70% inside the red cells in less than 5 minutes. (See Example III). Based on these results, Tc-99m-PnAO and various derivatives or other tetradentate amine oximes (e.g., EnAO derivatives) maintain the greatest potential of any known Tc-99m-chelates that could be used as a radiopharmaceutical to assess patterns of regional cerebral blood flow (rCBF) in humans.

Tc-99m-PnAO (or Tc-99m EnAO) could be used to assess rCBF using commercially available Nuclear Medicine instrumentation which has the capability of following the rate of washout of activity (e.g., Xe-133) from various regions of the brain. For example, SPECT images can be obtained using a specialized Tomographic Unit (Tomomatic Model 64 Medimatic Corp, Irvine, CA) while the multiprobe system (Novo Cerebrograph marketed by Novo Laboratories, Inc., Wilton, CT) can be used to follow washout patterns in localized brain areas. Other PnAO derivatives can be made that form chelates with a higher extraction efficiency by increasing lipophilicity and may be as suitable or even more suitable than Tc-99m-PnAO for rCBF assessment using this instrumentation. Derivatives of the PnAO ligand that would be suitable for complexing Tc-99m and used in these types of rCBF studies include derivatives with alkyl groups attached to the C-2-propylene carbon of PnAO. These derivatives can be synthesized by the diethylmalonate route outlined earlier. The various substituents which may be attached to the C-2 carbon of the propylene group can be illustrated as follows:

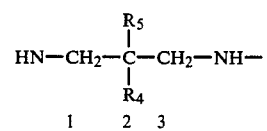

If the above portion of the structural formula, for propylene amine oxime and substituted derivatives thereof, the letter $R_4$ can be hydrogen (H) or possibly an alkyl group of 1–4 carbons. When $R_4$ is hydrogen, $R_5$, may be an alkyl or alkylene group of 1–20 carbons such as 2–8 carbons which comprise lipophilic groups. An example of a derivative of this type (i.e., $R_4=H$, $R_5=n-C_5H_9$) has been synthesized and found to form a single component-hydrophobic Tc-99m-complex (See Example IV). Alternatively, when $R_4$ is an alkyl group of 1–4 carbons, $R_5$ may be an alkyl group of 1–4 carbons. 1,3-diaminopropane derivatives disubstituted with small alkyl groups at the C-2 propylene are commercially available and can be used as starting materials.

An alternative way to form more hydrophobic 1,3-propane diamine derivatives is to attach small groups to the $C_1$ and $C_3$ carbons as illustrated below:

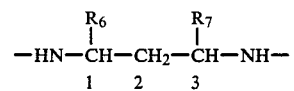

$R_6$ and $R_7$ are small alkyl groups from 1–4 carbons. These derivatives can be made by reacting $\alpha$-$\gamma$-diketones (e.g., acetylacetone) with $NH_3$, followed by reduction to produce the following 1-3-propane diamine derivatives and subsequent reaction with the chlorooxime reagents.

It is recognized that the overall lipophilicity of the PnAO analogues will be determined not only by the alkyl group attached to the propylene, but also the presence of H or small alkyl groups on the chloro-oxime reagent, that is used. By varying the lipophilic character of these compounds, the optimum structure can be identified that maximizes the extraction efficiency of the Tc-99m-chelate by brain tissue.

An alternative type of clinically useful rCBF agent is one that will passively diffuse across the intact BBB from the plasma and be retained intracellularly. The intracellular retention should be enough to permit imaging by conventional SPECT instrumentation (e.g., Siemans Rotocamera, Siemans Corp., Iselin, N.J. or Meaga 500 Camera, Technicare Corp., Solon, Ohio). The Tc-99m-PnAO chelates proposed for this use are structural analogues of the I-123m-iodophenyl alkylamine derivatives. Specifically, Compound A, first described by Kung, et al., (3) and Compound B, described by Winchell et al., (4) have been proven to be useful rCBF imaging agents (I in each Structure=I-123).

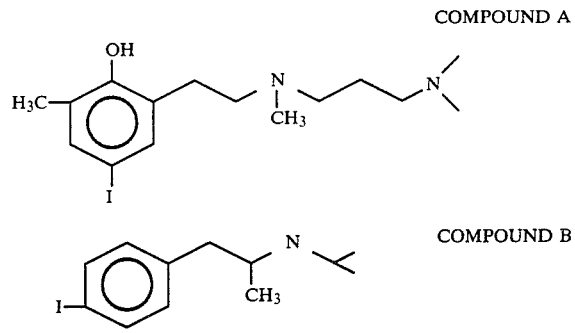

COMPOUND A

COMPOUND B

The Tc-99m-PnAO chelates that will be useful for this purpose will in essence be designed to replace the I-123-phenyl substituent with the neutral-lipophilic Tc-99m-PnAO (or a PnAO analogue) substituent using the same or similar side chains attached as shown for Compounds A & B. The most straight forward method to attach substituents to PnAO (or one of its analogues) is to attach the chain to the C-2 propylene by the diethylmalonate synthetic route described earlier. The substituent, attached either directly to or via an ether linkage to the C-2 propylene will be an alkyl amine or polyamine chain that may contain from 4–10 carbons. If the polyamine and alkyl amine chains that are attached to the phenyl ring in Compound A & B, respectively, are attached to PnAO (or a suitable analogue), they should produce a very desirable rCBF imaging agent. However, other alkyl amine and poly amine groups attached to PnAO may be superior. For examples of such side chains See Winchell et al., (23).

Two examples of synthesis using the diethylmalonate synthetic route are outlined as follows: The PnAO analogue with a structure similar to Compound A can be prepared by reacting 2-(cyanoethyl)diethylmalonate (Aldrich 15, 956-5) with ammonia and subsequent reduction with sodium borohydride to form 2-(ethylamine)malondiamide. This compound can then be reacted with ClCH$_2$CH$_2$CH$_2$N(CH$_3$)$_2$·HCl (Aldrich D14, 520-3) and then reduced with diborane to form the 1,3-propanediamine derivative. One part of this propane diamine derivative is then reacted with two parts of a chloro-oxime reagent to produce the desired PnAO derivative.

The second example involves reaction of the preformed Br-alkyl amine salt (i.e., BrCH$_2$CH(CH$_3$)NHCH(CH$_3$)$_2$·HBr) with diethyl malonate followed by amidation, reduction with diborane and subsequent reaction of the 1,3-diamino propane derivative with a chloro-oxime reagent.

Myocardial Imaging Agents

Fatty acid analogues labeled with I-123 have been shown to be effective for myocardial imaging in humans. Myocardial uptake and oxidative metabolism of these compounds is not critically dependent upon subtle structural differences. In fact, long chain fatty acid analogues that have bulky I-123-phenyl groups attached to the ω-end by a variety of linking groups are taken up by heart muscle (24). For this reason, replacement of the I-123-phenyl substituent with Tc-99m-PnAO (or a Tc-99m PnAO analogue) should produce an agent with similar myocardial uptake because of the exceptional ease in which this neutral-hydrophobic chelate passes through biological membranes. Fatty acid analogues with PnAO attached to the ω-end, having the structure indicated below can be made using the diethyl malonate synthetic route outlined earlier (See Example V). Once the 1,3-diamino propane derivatives have been made, PnAO, or PnAO analogues can be produced by reacting them with one of the chloro-oxime reagents.

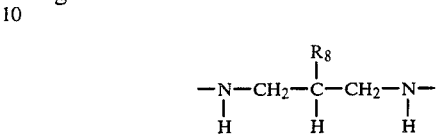

$R_8$ is a fatty acid analogue attached either directly to or by an ether linkage to the propylene C-2 atom. Thus $R_8$=—CH$_2$—X—COOH or —O—X—COOH where X is a linear alkane or alkene group with 6-22 carbons. For example, Tc-99m-PnAO-hexadecanoic acid (where X=—(CH$_2$)$_{15}$) is an exact analogue of ω-I-123-phenyl-hexadecanoic acid which is known to localize in myocardial tissue (24). This general type of compound where X is a linear chain is taken up rapidly by heart muscle and clears because of β-oxidation (25). By following the rate of regional myocardial clearance, one can obtain a localized oxidative myocardial metabolic index. A variety of atoms or groups can be used to link the fatty acid analogue side chains to the tetradentate amine oxime chelating moiety. Lin et al., (24) showed that attaching the I-123-phenyl group to the ω-end of several fatty acid analogues with ether, amide, ester, thioether, amine, and sulfonimide linkages did not significantly alter their uptake in the myocardium of rats.

Several structural modifications have been made to trap I-123 labeled fatty acid analogues in heart muscle to permit planar and tomographic imaging over extended times. Similar modifications can be made for the ω-PnAO fatty acid derivatives. For example, Livini et al., (26) showed that the addition of a methyl group to the β-position on a ω-I-131-phenyl fatty acid anlogue (i.e., ω-I-131-phenyl-b-methyltetradecanoic acid) produced a derivative that concentrates in normal myocardium and has a retention time sufficiently long to permit conventional SPECT imaging. A labeled fatty acid analogue, such as this, that is partially metabolized in the myocardium would be very useful for imaging regional metabolism in the heart. The addition of the small alkyl side chain in the β-position inhibits beta-oxidation of fatty acids (12). Thus, ω-Tc-99m-PnAO-with a alkyl substitution in the C-3 position (as shown below) should behave in vivo in a manner similar to the β-methyl-ω-I-123-phenyl fatty acid derivatives and find wide spread applicability for metabolic imaging of the myocardium.

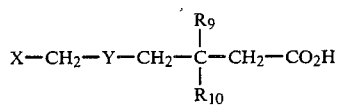

X = Tc-99m-PnAO

The letter $R_9$ can be hydrogen (H) or a small alkyl group of 1-3 carbons. $R_{10}$ is an alkyl group of 1-3 carbons when $R_9$ is either a hydrogen or alkyl group. Y is an alkyl or alkylene chain of 5-19 carbons atoms. As before, numerous groups to link a fatty acid analogue to the C-2 propylene onto PnAO or its analogues can be used (e.g., ether, amide, etc.). Furthermore, one or two alkyl groups can be added to carbon atoms on the fatty acid chain other than at the β-position which will cause metabolic trapping. To interrupt β-oxidation, the alkyl groups must be on carbon atoms which are multiplets of 2 away from the β-carbon. Alternatively, insertion of a Tc atom in the fatty acid side chain will cause intramyocardial trapping (14). The synthetic approches used to synthesize the Te- (27) and β—CH$_3$— fatty acid derivatives (12, 26, 28) can be used to produce the PnAO fatty acid derivatives.

It is essential to recognize that fatty acid analogues have limited solubility in aqueous solutions. Therefore, the feasibility of producing "kit" type formulations for routine human use demands that the Tc-99m-chelating group attached to the ω-end of these analogues be able to form a stable chelate in high yields at low concentrations at or near neutral pH. The linear tetradentate amine oxime ligand (e.g., PnAO) is capable of forming >95% yields at $3 \times 10^{-5}$ M (See Example II, Table 1). Because of this property, this type of ligand, as far as known, is the only one that will allow the production of a wide variety of Tc-99m-labelled fatty acid analogues with a stable-neutral-lipophilic chelate at the ω-end by "kit"-type formulation.

Lung Imaging Agents

Tc-99m lableled compounds that are extracted from plasma by lung tissue may be useful in assessing various lung diseases. Tc-99m-PnAO has demonstrated significant lung tissue localization. (See Example III).

Because Tc-99m-PnAO clears the blood and does not accumulate significantly in heart muscle, the lung/blood and lung/heart ratios are both approximately 10/1 at 15 sec post injection (these ratios are high enough to permit good lung imaging). All of the Tc-99m complexes of PnAO or the derivatives to (PnAO analogues) that were outlined for use in brain images can also be used to assess lung disease. The alkyl derivatives (used to measure rCBF patterns by determining regional brain clearance) can be used to assess lung diseases where the uptake and washout of a neutral-lipophilic Tc-99m-pharmaceutical is required (e.g., to determine differences in extravascular lung water (6)). Tc-99m-PnAO, in its underivatized form should be suitable for these studies.

The alkyl amine and polyamine derivatives proposed for brain imaging which are retained long enough for imaging with conventional SPECT instrumentation (e.g., Tc-99m-chelate analogues of Compounds A and B) can also be used. These latter types of compounds would have lengthened lung retention (similar to Compound B(7)) because of their apparent binding to high-affinity amine binding sites located on the membranes of pulmonary endothelial cells (7,29). This type of Tc-99m compound could provide a method to routinely evaluate the metabolic function of the lung, especially the lungs effect on concentration of circulating bioamines (29). As previously stated, the tetradentate amine oxime ligand provides a unique opportunity to produce "kit"-type formulations of Tc-99m-labeled compounds for both brain and lung-imaging in clinical Nuclear Medicine.

EnAO will also form a neutral-lipophilic stable Tc-99m complex that passively diffuses across the intact BBB and other lipid-bilayer membranes. Accordingly, derivatized forms of EnAO with various substituents attached to the tetradentate ligand back bone, similar to the structures proposed for PnAO derivatization, can be synthesized. The only difference would be that substituents are attached to either one or both ethylene carbons instead of the propylene carbons in PnAO.

These derivatives can be made by forming ethylene diamine derivatives as outlined below:

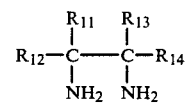

The ethylene diamine derivatives will react with a chloro-oxime reagent to form various substituted EnAO ligands. For example, $R_{11}$ can be a fatty acid analogue side chain of 6 to 22 carbons linked by various groups (e.g. amides, ethers, etc.) with $R_{12}$, $R_{13}$, and $R_{14}$ being H atoms or one or more small (1-3 carbons) alkyl groups. $R_{11}$ and $R_{13}$ can be small alkyl side chains (1-5 carbons) with $R_{12}$ and $R_{14}$ equal to hydrogen (H) and formed using α-β diketones. Alternatively, $R_{11}$ can be an alkyl or polyamine chain (with only secondary or tertinary amines). Tc-99m complexes of EnAO derivatives should have the same in vivo behavior as the analogous Tc-99m-PnAO derivatives.

PnAO does not appear to be toxic. Swiss-Webster mice injected intravenously with approximately 1000-1500 times the anticipated mg/kg dose for humans showed no measurable or visible acute effects (see Example VI). This implies that these types of ligands, their derivatives and their Tc-99m-chelates will be safe to use in diagnostic Nuclear Medicine Procedures.

EXAMPLE I

Preparation of Tc-PnAO solutions from Tc-99m

Two mg of PnAO was dissolved in 0.1 ml of $10^{-3}$-$10^{-4}$M HCl (i.e., pH 3-4) and then brought to a pH of ~8 by dropwise addition of 0.1M NaOH. To this solution was added 0.7 ml of Tc-99m (7 to 30 mCi as NaTcO$_4$) followed by 0.1 ml of SnC$_4$H$_4$O$_6$ ($10^{-4}$M).

This resulted in a ligand concentration of $3.5 \times 10^{-4}$M. The solution was slurried or shaken and allowed to stand for 10 to 30 minutes. In some experiments dilution with saline or with acetate or bicarbonate buffers was used to study the effects of changes in ligand concentration or pH. Tc-99 ($5 \times 10^{-7}$M or $5 \times 10^{-6}$M NH$_4$TcO$_4$) was also used to prepare Tc-99-PnAO.

As an alternate method, 2 mg of PnAO was slurried with 0.9 ml Tc-99m and 0.1 ml SnC$_4$H$_4$O$_6$ and held for 20 minutes at 80° C. The mixture was cooled and filtered.

Preparation of Solid Tc-PnAO from Tc-99

A solution prepared from 10 ml $10^{-2}$M PnAO in $10^{-3}$ HCl, 1 ml of $2.8 \times 10^{-2}$M NH$_4$TcO$_4$(Tc-99), 1 ml generator-produced NaTcO$_4$ (1mCi Tc-99m) as a tracer, and 2 ml 1 M NaHCO$_3$ was mixed and heated at 80° C. Three 0.2-ml portions of $10^{-1}$M SnCl$_2$ were added at 20 minute intervals. A solid and an orange-brown solution resulted.

The solid was extracted with CH$_3$OH. Two drops of water were added to two ml of this extract and allowed to evaporate slowly. After four days, orange-red crystals appeared and one was selected for an x-ray diffraction structural study.

EXAMPLE II

The foregoing compounds were subjected to test procedures which included high performance liquid chromatography (HPLC), ascending solvent paper chromatography (PC), electrophoresis and solvent extraction. Crystal structure of solid Tc-PnAO was determined by x-ray diffraction.

HPLC Separations

HPLC separations were done on a Hamilton PRP-1 column with a Beckman Series 332 dual pump gradient chromatograph system. The radioactivity in the eluent was detected by a NaI scintillation detector connected to a ratemeter. The signal from the ratemeter was directed to a Houston Instrument Co. Omniscribe B-5000 strip chart recorder and to a Hewlett-Packard Model 3390A integrator.

The liquid phase at the beginning of separation was 0.02M $NaH_2PO_4$ containing 2% $CH_3OH$. One-half minute after the injection of a 10-microliter sample, THF was added at a gradient such that its volume % was 25 at 3.5 min. Elution was continued at that concentration until 8.0 min, at which time the liquid phase was restored to 2% $CH_3OH$ to equilibrate the column for the next separation. Flow rate was 2 ml/min for all phases of the separation. Reduced, hydrolysed Tc eluted at 0.7 min, $TcO_4^-$ at 1.1 min, and the complex at 6.5 min. Percentage complex yields were determined from the areas under the peaks as measured by the integrator. The hydrophobicity of the complex is demonstrated by the necessity of using an organic solvent to elute it.

Paper Chromatography and Electrophoresis

An alternate method of analysis employed the results of paper chromatography and electrophoresis.

Paper strips (5×120 mm cut from Gelman saturation pads) were spotted with 5 microliters of sample 1 cm from the bottom of the strip and developed with acetone and with saline. The solvent front was allowed to ascend to the top of the strip. The strip was cut into six 2-cm sections and the Tc-99m in each determined by counting in a NaI well counter. Electrophoresis was carried out with a Gelman Deluxe Power Supply and Chamber using 0.1M $NaHCO_3$ buffer at pH 8.5 and Beckman #320046 electrophoresis strips at 300 volts for 45 or 60 min. The strips were scanned with a Technical Associates scanner or cut into sections as above.

The percentage of $TcO_{4-99m}^-$ and reduced Tc-99m can be determined from the activity in the electrophoresis anode peak and the saline paper chromatography origin section, respectively. A large electrophoresis peak at the origin in the absence of reduced Tc is evidence for a neutral complex.

Octanol/saline and $CHCl_3$/saline separations

Fifty microliters of a Tc-99m-PnAO complex prepared by one of the methods above was added to 5 ml of normal saline and the solution thoroughly mixed. One ml of this solution was added to 1 ml of n-octanol and vortexed for 1 min and then centrifuged for 5 min. Ten-microliter aliquots were withdrawn from each layer and counted in a NaI well scintillatin counter. An 0.8-ml aliquot of the octanol layer was withdrawn and added to an equal volume of normal saline and the extraction and counting repeated as above. The results of this back extraction were used to compute the octanol/saline ratio. Similar experiments were done with $CHCl_3$/saline as an approximate measure of complex yield. A high extraction ratio into these solvents indicates hydrophobity of the complex.

Results

The effect of concentrations of $TcO_4^-$, PnAO, and $SnC_4H_4O_6$ on the complex yield is shown in Table 1.

TABLE 1

Effect of concentrations on complex yield.

| $[TcO_4^-]$ | [PnAO] | $[SnC_4H_4O_6]$ | Yield (%) |
|---|---|---|---|
| Tc-99m | $3 \times 10^{-3}$ | $1 \times 10^{-5}$ | 98 |
| Tc-99m | $3 \times 10^{-4}$ | $1 \times 10^{-5}$ | 99 |
| Tc-99m | $3 \times 10^{-5}$ | $1 \times 10^{-5}$ | 95 |
| Tc-99m | $3 \times 10^{-6}$ | $1 \times 10^{-5}$ | 93 |
| Tc-99m | $5 \times 10^{-5}$ | $1 \times 10^{-6}$ | 98 |
| *$5 \times 10^{-7}$ | $5 \times 10^{-5}$ | $5 \times 10^{-6}$ | 97 |
| *$5 \times 10^{-6}$ | a | $2 \times 10^{-5}$ | 98 |

Tc-99m concentrations were in the range (0.4–2) $\times 10^{-7}$ M.
*Tc-99 was used for these studies.
Complex yields were measured 30 min after preparation using HPLC.
a Saturated solution of PnAO at 50° C.

This demonstrates that the complex can be formed in high yield at $TcO_4^-$ concentrations equivalent to those normally encounted from commercial Mo-99-Tc-99m generators and low concentrations of PnAO and reducing agent.

The effect of pH on complex formations is shown in Table 2. Yields were measured 30 minutes after complex formation.

TABLE 2

Complex Yield as a Function of pH

| pH | Yield (%) | pH | Yield (%) |
|---|---|---|---|
| 3.2 | 76 | 8.5 | 98 |
| 4.0 | 85 | 10.0 | 98 |
| 5.5 | 92 | 11.0 | 91 |
| 7.0 | 98 | 12.0 | 80 |

The effect of pH on the stability of the complex stored in air is shown in Table 3. Complexes were prepared at pH 8.5 and then adjusted to the pH's shown. All were at least 98% complexed at the time of formation.

TABLE 3

Effect of pH on Complex Stability

| | Complex Yields (%) | | |
|---|---|---|---|
| pH | 1 hr | 2 hr | 24 hr |
| 3.2 | 96 | 81 | 59 |
| 4.0 | 92 | 80 | 63 |
| 5.5 | 98 | 97 | 98 |
| 7.0 | 99 | — | — |
| 8.5 | 100 | 98 | 95 |
| 10.0 | 99 | 97 | 95 |
| 11.0 | 71 | 34 | 0 |
| 12.0 | 14 | 0 | 0 |

The complex can be formed in high yield over the pH range 5.5 to 10 and is stable up to 24 hours at those same pH's. It was also found that complexes prepared at pH 8.5 and diluted by a factor of 1000 with normal saline were also stable for 24 hr.

Validation that the complex is neutral and formed in high yields is demonstrated by the results in Table 4.

TABLE 4

Paper Chromatography and Electrophoresis of Tc—PnAO, TcO$_4^-$ and reduced Hydrolysed Tc. (Tc = both Tc-99 and Tc-99m).

| | Tc—PnAO | TcO$_4^-$ | Red. Tc |
|---|---|---|---|
| % Activity at origin in paper chromatography | | | |
| Acetone | ~2 | <1 | ~100 |
| Saline | <1 | <1 | ~100 |
| Migration distance in electrophoresis, cm | | | |
| Anode | 0 | ~8 | 0 |
| Cathode | 0 | — | 0 |
| Activity at origin in electrophoresis | >97 | <1 | 100 |

There is a large peak at the electrophoresis origin; which is not reduced Tc-99m (shown by paper chromotography), and is therefore the comlex which must be neutral. Further proof of the hydrophobicity is that the octanol/saline extraction ratio for Tc-PnAO (average of 5 trials) is 11±3 and the CHCl$_3$/saline extraction ratio is 29±5.

Tc-EnAO and Tc-BnAO complexes with Tc-99m

Complexes of EnAO and BnAO were also prepared by the methods above. Results are summarized in Table 5.

TABLE 5

Yields and extraction ratios of Tc-99m complexes with EnAO, PnAO, and BnAO

| Complex | Percent Yield[a] | Octanol/Saline Extraction Ratio | CHCl$_3$/Saline Extraction Ratio |
|---|---|---|---|
| Tc-99m-EnAO | >95% | 3.4 | 21 |
| Tc-99m-PnAO | >95% | 11 ± 3 | 29 ± 5 |
| Tc-99m-BnAO | >95% | 0.17 ± 0.04 | 1.04 ± 0.13 |

[a]Prepared as described above at pH 8.1 and ligand concentrations ranging from $10^{-4}$ to $5 \times 10^{-2}$ M.

Structure of Solid Tc-PnAO with Tc-99

Structure of solid Tc-PnAO was determined by x-ray diffraction using data collected on an Enraf-Nonius CAD4 diffractometer. The structure solution was accomplished using the SDP program package of Enraf-Nonius on a PDP 11/34 computer and has been refined to a current agreement factor of 2.8%.

The structure described above is consistent with the chemical formula TcC$_{13}$H$_{25}$N$_4$O$_3$ or [TcO(PnAO-3H)]° where the -3H represents the loss of three H atoms from the PnAO ligand, one from an oxime oxygen and two from the amine nitrogens. The Tc is in the +5 oxidation state resulting in a net charge of zero for the ligand.

A sample of the solid was dissolved in CH$_3$OH and subjected to electrophoresis and paper chromotography. The results indicated a complex yield of greater than 95%, consistent with that of the complexes formed with Tc-99m.

EXAMPLE III

Biolocalization Properties of Tc-99m-PnAO

The in vivo stability of Tc-99m-PnAO appears to be excellent. A 0.1 ml sample of Tc-99m-PnAO was added to human serum and allowed to stand in air for 8 hours. After 8 hrs the HPLC analysis demonstrated that >95% of the chelate remained. All HPLC analyses of Tc-99m samples were performed in the manner described in Example II. Bile and urine samples were collected from anesthesized 300–350 g rats. Bile samples were collected for 30 min (via a cannula placed in the common bile duct) after IV injection of Tc-99m-PnAO. The urine and bile from these rats were analyzed by HPLC. It was found that >90% of the Tc-99m activity in either the bile or urine was still complexed to PnAO. These data suggest that Tc-99m is quite stable in the body and body fluids.

Tc-99m-PnAO will diffuse across the cellular walls. This is demonstrated by the observation (Table 6) that a 0.1 ml sample containing this chelate when added to whole blood (Hct=45) will localize in red cells (RBC's). After only five minutes of mixing 64.9±1.9% of the activity was found in the RBC fraction. Longer mixing times did not change this percentage. When the blood was centifuged, the plasma removed and the cells (Hct=45) resuspended in saline, 70.2+3.1% was found in the RBC's after only 5 minutes indicating redistribution of the Tc-99m chelate inside and out of the RBC's. A second wash with saline resulted in the same intracellular/extracellular ratio (Table 6). This data demonstrates that Tc-99m-PnAO will diffuse through RBC outer membranes and, further, that the activity can be washed out of the RBC's.

TABLE 6

Percent Tc-99m-PnAO Associated with Red Blood Cells (Hematocrit-.45) at 22° C.

| Medium | Percent Complex in RBC Fraction |
|---|---|
| Whole Blood | 64.9 ± 1.9 |
| After First Saline Wash | 70.2 ± 3.1 |
| After Second Saline Wash | 73.8 ± 2.1 |

The blood clearance of Tc-99m-PnAO was performed in rats (curves not shown). Table 7 shows that less than 7% of the dose remains in the blood stream one minute after IV injection. This table also shows that at five and fifteen seconds following injection the uptake of this chelate in the brain is high. By comparison, the uptake of a hydrophilic chelate (e.g., Tc-99m-DTPA) in the brain of rats is a factor of at least ten less.

TABLE 7

Uptake of Tc-99m-PnAO as a fraction of time after a 1 cc bolus injection into the jugular vein of rats.

| | 5 sec. | | 15 sec. | | 1 min. | | 10 min. | |
|---|---|---|---|---|---|---|---|---|
| ORGAN | % D | % D/gm | % D | % D/gm | % D | % D/gm | % D | % D/gm |
| Brain | 1.2 ± .3 | .68 ± .12 | 1.3 ± .09 | 0.69 ± .04 | 0.97 ± .15 | 0.54 ± .09 | 0.22 ± .03 | 0.12 ± .01 |
| Lung | 6.6 ± 1.4 | 6.0 ± 1.5 | 6.9 ± 1.3 | 5.6 ± 1.1 | 5.71 ± .76 | 4.0 ± .9 | 1.8 ± .5 | 1.7 ± .4 |
| Heart | 0.56 ± .13 | .77 ± .24 | 0.4 ± .08 | 0.58 ± .09 | 0.34 ± .04 | 0.43 ± .08 | 0.17 ± .25 | 0.25 ± .06 |
| Blood | 8.9 ± 1.9 | 0.59 ± .11 | 8.11 ± 1.5 | 0.50 ± .10 | 5.3 ± 1.1 | 0.34 ± .09 | 5.9 ± .76 | 0.46 ± .08 |

Rats (260–300 gm) were anesthesized with 50 mg/kg of pentobarbital. A fifty microliter bolus was injected into the jugular vein and the animals (5 in each group) decapitated at 5 sec, 15 sec, 1 min and 10 min after injection.

As time progresses the % D and % D/gm of Tc-99m activity in the brain decreases demonstrating that this chelate washes out (similar to washout from RBC's) of the tissue.

The uptake and washout of Tc-99m-PnAO by the brain in laboratory animals was clearly demonstrated by two other techniques.

A. First, three different laboratory animals (rats, rabbits and dogs) were positioned under an Ohio-Nuclear Model 120, Mobile Scintillation Camera coupled to a PDP 11/40 computer such that only the head and neck area were visualized. A bolus injection of 0.5–2 mCi of Tc-99m-DTPA was first injected into the femoral vien of each anesthesized animal. The digitized scintiphotos showed comparatively little activity in the brain area compared to surrounding tissue, or precisely what is observed in Tc-99m-DTPA brain scans in humans. Brain visualization does not occur since Tc-99m-DTPA is hydrophilic and will not diffuse across the blood-brain barrier (BBB).

Fifteen minutes after the Tc-99m DTPA injection, 1–5 mCi of Tc-99m-PnAO was injected into each animal. In these experiments, the brain in each animal could be clearly visualized shortly after injection and showed more activity in the brain than surrounding tissues. Fifteen minutes after injection, the brain activity had decreased to a level below the surrounding tissue, indicating washout of the activity from the brain which is consistent with the data in Table 7.

Regions of interest (ROI's) over the brain and non-brain soft tissue were defined on the digitized images and time-activity curves generated. The time-activity curve in the brain ROI following Tc-99m-DTPA injection showed a sharp spike of Tc-99m activity crossing the brain in a few seconds. However, the brain time activity curve for Tc-99m-PnAO showed almost total uptake at approximately five seconds after a relatively slow biphasic washout. These biphasic curves were similar to those observed for the washout of Xe-133 activity from the brain in humans (21). These results demonstrate that Tc-99m-PnAO is efficiently extracted from the blood by the brain and washes out of brain tissue at a rate similar to that observed for Xe-133. Furthermore, the rate of regional brain washout should be proportionate to rCBF making it possible to determine rCBF patterns in humans using commercially available instrumentation.

B. The second technique involves the utilization of a remote single probe system that is constructed similar to that described by Raichle et al., (22) to estimate extraction efficiency of various compounds by brain tissue. This system consists of a single gamma ray detection system (with a 1-hole collimatar) connected to a multi-channel analyzer operated on the multiscalar mode. The anesthesized animal was positioned on the probe so that the brain was directly over the 1/8" hole through the collimator. A bolus injection of Tc-99m-PnAO was made into the internal carotid artery. The bolus was delivered in <0.5 seconds through a 30 ga. needle so as not to impede blood flow. The activity/0.1 sec counted by the probe was plotted as a function of time for approximately ten minutes. The extraction efficiency determined by this method was estimated to equal approximately 70–90% in both rats and rabbits.

The same study was also performed using the monkey model of Raichle et al., (22). The extraction efficiency of Tc-99m-PnAO and rate of clearance was compared to that for O-15-H$_2$O in the same animal at three different brain-blood flows. The extraction efficiency of Tc-99m-PnAO was determined to be 80% at normal blood flow (i.e., 55 ml/100g-min). The rate of clearance from the brain in the monkey in the first 3 minutes after intracarotid injection was not significantly different than the 15-O-H$_2$O clearance rate (the first linear portion had a t$_{\frac{1}{2}}$ of ~25 sec). It is clear from these results (and those using the digitized images of Tc-99m-PnAO uptake and washout) that the extraction of Tc-99m-PnAO by brain is efficient. In fact, as far as it is known, this complex is extracted more efficiently by brain tissue than any other Tc-99m chelate.

Lung uptake was also found to be high. At 15 sec approximately 6% injected dose/gm is observed in rats. The washout rate from the lungs is slower than brain and 4.0±0.9% is left after one minute. The blood activity, by comparison, is low with the lung/blood ratio of 11.2 and 11.8 at 15 seconds and 1 min, respectively, after carotid injection into rats. The lung/heart rates are also high at 9.7 and 9.3 at 15 sec and 1 minute, post injection respectively. These data indicate that Tc-99m-PnAO would make an excellent lung imaging agent. Scintiphotos of laboratory animals injected IV with this chelate show good quality planar images with good contrast between the lung and heart. Time-activity curves on anterior or posterior images using computerized regions of interest from computerized lung images can be generated.

Tc-99m-PnAO is eliminated from the blood primarily by the liver. Table 8 shows the tissue distribution of this chelate in mice at 15, 30, 60 and 120 min after tail vein injection. By 15 min the total liver and small intestine activity account for 51% of the injected activity and by 120 min the Tc-99m in the intestines and liver accounts for 68% of the activity. Most of the Tc-99m-PnAO removed from circulation by the liver is rapidly transported into the bilinary system. There is less but significant elimination of the complex through the kidneys. Approximately 20% Tc-99m-PnAO is found in the urine at 120 min post-injection. Even at 15 and 30 min the % ID/gm of Tc-99m activity in the lungs is high while the brain activity is <1% ID at 15 min and longer. This latter observation is consistent with the results with other species where the Tc-99mPnAO activity has been largely washed out of brain tissue within 15 min.

Tc-99m-EnAO has been prepared in the same method outlined in Example I for Tc-99m-PnAO. Tc-99m activity from this preparation has a CHCl$_3$/saline extraction ratio of 21 and was found to have a neutral charge by electrophoresis. The octanol/saline partition coefficient of the preparation was found to be 3.4. Using the external probe, the Tc-99m-EnAO preparation was shown to be extracted by brain tissue in rats with an efficiency, similar, but slightly lower than Tc-99m-PnAO. This experiment shows that Tc-99m-EnAO can also be used to form a neutral-hydrophobic chelate capable of penetrating the blood-brain-barrier. The time scale of Tc-99m-EnAO washout from the brain is also similar to that observed for Tc-99m-PnAO.

EXAMPLE IV

Synthesis of 2,2'-(1.3-diamino-2-pentyl-propane)-bis(2-methyl-3-butanone)dioxime and its complexation with Tc-99m a. 2-Pentyl diethylmalonate (I)

One gram sodium was dissolved in 10 ml of freshly distilled absolute ethanol. To this solution was added 7 ml of freshly distilled diethylmalonate. This suspension was heated to 70° C. for two hours. To the collected suspension was added 5.5 ml of freshly-distilled bromopentane. The resulting mixture was slowly heated to reflux overnight. Ethanol was distilled from the mixture and the product collected by vacuum distillation (78° C.-86° C. at 4.5 mm Hg) Yield=4.5 ml.

Mass spectrum, m/e=230 (M+).

NMR (60, MHz, CDCl$_3$), 0.8(t,3H),1.1(t,12H),1.7(broad signal,2H),3.1(t,1H),4.1(9,4H). (In this and following examples NMR data are in ppm and IR data in cm$^1$).

b. 2-Pentylmalondiamide (II)

Five grams of the above ester(I) was dissolved in methanol (25 ml) and a solution of ammonia in methanol(50 ml of a solution saturated at 0° C.) containing sodium methylate (from 50 mg sodium). The mixture was stirred at room temperature for 90 hours. A white precipitate was collected after exhaustive washing with hot methanol. Yield=70%. M.P.=185° C. Mass spectrum, m/e=172 (M+).

IR, 3450, 3374 (N—H); 1690 (C=O), 1600 (N—H)

NMR (60 MHz, DMSO-d$_6$), 0.8(t,3H), 1.1(m,6H), 1.6(br. signal, 2H), 7(s,br,2H), 7.2(s,br,2H).

c. 2-chloro-2-methyl-3-butanone oxime (III) was synthesized by the method of Murmann (J. Am. Chem. Soc. 79, 521 (1957)).

d. 2-Pentylpropanediamine (IV)

Two grams of (III) was suspended in 40 ml freshly distilled THF. The suspension was cooled to 0° C. and 40 ml of diborane: THF complex was gradually added. The suspension was stirred at room temperature for about 20 hours and the temperature then raised to reflux. After one hour of reflux, the resulting suspension was cooled to room temperature and 10 ml of 5N HCl was added. The THF was removed by distillation. The resulting thick residue was saturated with sodium hydroxide pellets and the suspension extracted with petroleum ether. The ether extract was washed with water and dried over sodium sulfate. The product was examined by TLC using a plate developed with methanol ammonium hydroxide (100:1) and stained with copper sulfate. A single blue spot developed upon mild heating.

IR, 3400,3300 (N—H), 1670,1600 (N—H)

NMR (60 MHz, CDCl$_3$), 0.8(t,br,3H), 1.1(s,br,8H), 1.6(br,1H), 2.5(br,4H), 3.5(br,4H).

e. 2,2'-(1,3-diamino-2-pentylpropane)bis(2-methyl-3-butanone)oxime (V)

140 mg of (IV) was dissolved in 5 ml of freshly distilled methanol and 290 mg of (III) was added. The resulting mixture was held at 0° C. for 2 hours and then brought to room temperature. After 2 hours at room temperature, the mixture was refluxed overnight. The resulting solution was concentrated under reduced pressure and suspended in chloroform. This suspension was filtered and the filtrate examined by TLC as above. One green spot with R$_f$ greater than that for (IV) was developed. IR 3250 (O—H), 1675 (C=N), 1600 (N—H).

NMR (60 MHz,CDCl$_3$), 0.8(t), 1.1(s,br), 1.3(s,br), 1.8(s,br), 2.3(m,br), 3.0(br), 3.5(m,br), 9(d,br).

This ligand (V) was then complexed with Tc-99m by the method outlined in Example I.

A complexation yield of 90±5% was obtained and a single hydrophobic peak was observed during HPLC analysis. The retention volume of this Tc-99m-n-pentyl-PnAO derivative is larger than that of Tc-99m-PnAO using the gradient elution HPLC method described in Example II indicating that this derivative, as expected, has a higher hydropobicity than Tc-99m-PnAO.

EXAMPLE V

Synthesis of 2,2'-(1,3-diamino-2-(hexadecanoic acid) propane) bis (2-methyl-3-butanone) dioxime a. Synthesis of 16-bromohexadecanoic acid (VI)

Ten grams of 16-hydroxydecanoic acid was dissolved in 100 ml of 30% hydrobromic acid in glacial acetic acid and refluxed for 6 hours. The mixture was dried under reduced pressure and finally vacuum distilled at 100° C. (4.8 mm Hg). The residue of the distillation product was crystallized from petroleum ether. Yield 90%. m.p. 69°-69.5° C.

IR(neat), 1675 (C=O)

NMR (60 MHz, CDCl$_3$), 1.5(s,br,Ch$_2$), 2.3(m,CH$_2$—C=O), 3.4(t,CH$_2$-br), 9(br,COOH).

b. Synthesis of 2-(hexadecanoic acid)-diethyl malonate. (VII)

One gram of sodium metal was dissolved in 15 ml of freshly distilled absolute ethanol. Seven grams of diethyl malonate was then added to the cooled solution of sodium ethoxide. The resulting suspension was refluxed for one hour and cooled to room temperature. Two grams of 16-bromohexadecanoic acid was added and the suspension refluxed overnight. The suspension was cooled and filtered after evaporation of most of the ethanol. The resulting white precipitate was exhaustively washed with cold ethanol.

IR(neat), 1750(—C=O),ester), 1710 (—C=O, acid)

NMR (60 Mhz, CDCl$_3$), 1.2 to 1.5(s,br, CH$_2$), 2.3(m, CH$_2$—C=O)   3.2(m, O=C—CH—C=O), 3.4(m, CH$_2$—Br),   4.1(g, —CH$_2$—O—C=O).

c. Synthesis of 2-(ammonium hexadecanoate)malondiamide 2.65 grams of 2-(hexadecanoic acid)diethyl malonate was suspended in 100 ml of freshly distilled methanol saturated with ammonia at 0° C. To this suspension was added 200 mg sodium in a solution of methanol and the resulting mixture stirred at room temperature for eighty hours. The product was recovered from boiling methanol by filtraton. m.p. 225° C.-230° C.

IR(nujol mull), 3400, 3200 (NH), 1700 (O=C—N),

1575(O=C—O—)

NMR(60 Mhz, DMSO-d$_6$), 1.2 to 1.5(CH$_2$), 2.3(m, —CH$_2$—C=O), 6.8 and 7.2(s, br, H$_2$N—C=O).
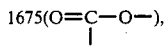

This doublet disappeared upon addition of D$_2$O.

Upon acidification of the above ammonium salt, the IR absorption at 1575 reappeared at 1675 and the m.p. changed to 184° C.–186° C.

d. Synthesis of 1,3-diamino-2(ammomium hexadecanoate) propane (IX).

500 mg of VIII was suspended in distilled THF and stirred for 1 hour under reflux. The suspension was cooled and 8 mL of 1M diborane: THF complex was gradually injected. The milkly suspension was stirred for 1 hour and then refluxed. All operations were carried out under nitrogen. After 3 hours, the reaction mixture was cooled and ice was added. The resulting suspension was acidified with 5N HCl and the THF distilled off. The pH was adjusted to 12 with ammonium hydroxide and the suspension filtered while hot. A white precipitate was collected after several washings with cold water. m.p. 117° C.–120° C.

IR(Nujol mull), 3400,3200(NH),

1675(O=C—O—),

1600(NH).

NMR (60 Mhz, DMSO-d$_6$), similar to that for III except for loss of doublet at 6.8,7.2).

e. Synthesis of 2,2′-(1,3-diamino-2(hexadecanoic acid) propane)bis(2-methyl-3-butanone)dioxime will be completed by adding 2-chloro-2-methyl-3-butanone oxime to IX as in Example IV.

EXAMPLE VI

Toxicity of Studies With PnAO

A solution consisting of 4 mg of PnAO/ml of physiological saline at pH 8.1 (0.01M HCO$_3$ buffer) was prepared for injection. Fifty microliters was injected into the tail vein of each of 10 unanesthesized Swiss-Webster mice weighing between 18–22 gms (corresponds to a dose in mg PnAO/kg body weight that is 1000–1500 times the anticipated dose to be administered to humans for diagnostic radionuclidic studies). A group of 10 Swiss-Webster mice in the same weight range were similarly injected with 50 microliters of physiological saline. Both groups were housed in the same animal quarters for 24 days, and the variation in body weight recorded 4 times each week. No significant difference was observed between the group which received the PnAO composition and the control group. No visual effects (e.g., seizures, abnormal behavior, etc.) were observed in any of the animals during or at any time after injection of either group. After observation for 24 days, no gross abnormality was observed in any of the organs taken after sacrifice. Thus, it is understood that the toxicity of PnAO is extremely low.

REFERENCES 21–29

21. J. Kanno and N. A. Lassen, J. Comp. Asst. 3, 71–76, 1979.
22. M. E. Raichle, et al., Am. J. Physiol., 230, 543–552, 1976.
23. H. S. Winchell, et al., J. Nucl. Med., 20, 940–946, 1980.
24. T. H. Lin, et al., Proc. Fourth Int'l Symp on Radiopharm. Chem., Julich, W. Ger., Aug. 23–27, 1982, pp. 44–45.
25. H. J. Machulla, et al., Eur. J. Nucl. Med., 5, 171–173, 1980.
26. E. Livini, et al., Third World Cong. Nucl. Med. and Biol., Paris, France, Aug. 31–Sept. 3, 1982, pp. 1684–1686.
27. F. F. Knapp, et al., J. Nucl. Med., 22, 988–993, 1981.
28. M. M. Goodman, et al., Fourth Int'l Symp. Radiopharm. Chem., Julich, W. Ger., Aug. 23–27, 1982, pp. 46–48.
29. T. F. Budinger, et al., J. Nucl. Med., 23, 60–65, 1982.

We claim:

1. The class of lipophilic macrocyclic complexes of technetium-99m (Tc-99m) useful as diagnostic radionuclides, said complexes being formed by complexing in aqueous solution technetium-99m pertechnetate (TcO$_4^-$-99m) under reducing conditions with an alkylene amine oxime containing from 2 to 4 carbons in the alkylene group, said complexes having a zero charge, containing an O—H—O ring closure bond, and being sufficiently stable for parenteral administration.

2. The macrocyclic complexes of claim 1 in which said oxime is propylene amine oxime.

3. The macrocyclic complexes of claim 1 in which said alkylene group is substituted with a lipophilic hydrocarbon group.

4. The macrocyclic complexes of claim 1 in which said alkylene group is substituted with a long chain fatty acid group containing from 6 to 22 carbons.

5. The complexes of claim 1 having a single oxygen bonded to the reduced Tc-99m.

6. The complexes of claim 1 in which said alkylene group is substituted by an alkyl amine or polyalkylamine group.

7. The macrocyclic complexes of claim 1 in which said oxime is ethylene amine oxime.

8. The macrocyclic complex of technetium-99m (Tc-99m) useful as a diagnostic radionuclide which is formed by complexing in aqueous solution technetium-99m pertechnetate (TcO$_4^-$-99m) under reducing conditions with 2,2′-(1,3-diaminopropane) bis(2-methyl-3-butanone) dioxime (PnAO), said complex having a zero charge, containing an O—H—O ring closure bond, having a single oxygen bonded to the reduced Tc-99m, and being stable in aqueous solution when exposed to oxygen.

* * * * *